United States Patent
Hengerer et al.

(10) Patent No.: US 10,459,045 B2
(45) Date of Patent: Oct. 29, 2019

(54) STERILE RF COILS FOR MR IMAGING SYSTEMS

(71) Applicants: Siemens Healthcare GmbH, Erlangen (DE); The Johns Hopkins University, Baltimore, MD (US)

(72) Inventors: Arne Hengerer, Möhrendorf (DE); Eva Rothgang, Nürnberg (DE); Lars Lauer, Neunkirchen (DE); Jonathan Lewin, Atlanta, GA (US); Jan Fritz, Baltimore, MD (US); Clifford Weiss, Baltimore, MD (US); Katarzyna J. Macura, Catonsville, MD (US); Paul Bottomley, Columbia, MD (US); Wesley David Gilson, Northbeach, MD (US)

(73) Assignees: Siemens Healthcare GmbH, Erlangen (DE); The Johns Hopkins University, Baltimore, MD (US)

( * ) Notice: Subject to any disclaimer, the term of this patent is extended or adjusted under 35 U.S.C. 154(b) by 572 days.

(21) Appl. No.: 15/082,048

(22) Filed: Mar. 28, 2016

(65) Prior Publication Data
US 2017/0276742 A1    Sep. 28, 2017

(51) Int. Cl.
| | | |
|---|---|---|
| *G01R 33/34* | (2006.01) | |
| *A61L 2/22* | (2006.01) | |
| *A61L 2/18* | (2006.01) | |

(52) U.S. Cl.
CPC .............. *G01R 33/34* (2013.01); *A61L 2/18* (2013.01); *A61L 2/22* (2013.01); *G01R 33/34007* (2013.01); *A61L 2202/24* (2013.01)

(58) Field of Classification Search
None
See application file for complete search history.

(56) References Cited

U.S. PATENT DOCUMENTS

| | | | |
|---|---|---|---|
| 5,091,442 A | 2/1992 | Milner | |
| 6,501,980 B1 | 12/2002 | Carlon et al. | |
| 6,832,108 B2 * | 12/2004 | deSouza | G01R 33/285 600/422 |
| 2003/0229319 A1 * | 12/2003 | Mitchnick | A61L 31/16 604/265 |
| 2004/0116551 A1 * | 6/2004 | Terry | A01N 59/16 523/122 |
| 2008/0129295 A1 * | 6/2008 | Carlton | G01R 33/341 324/318 |
| 2010/0062035 A1 | 3/2010 | Eggerstedt et al. | |
| 2015/0011870 A1 * | 1/2015 | Piferi | G01R 33/34 600/422 |

* cited by examiner

*Primary Examiner* — Douglas X Rodriguez

(57) ABSTRACT

Sterile RF coil arrangements for use in magnetic resonance imaging are provided. The sterile coil arrangements can be formed by spraying or coating a curable liquid onto an RF coil housing and allowing the liquid to cure or dry to form a continuous sterile layer on the coil housing. The thickness of the sterile layer can be between 100 and 1000 micrometers. The curable liquid can include an antimicrobial or antibacterial agent, such as silver ions or triclosan, to better maintain sterility of the coil arrangement. The curable liquid can be selected such that it adheres to the housing when cured and is also removable without leaving residue behind.

19 Claims, 2 Drawing Sheets

STERILE RF COILS FOR MR IMAGING SYSTEMS

FIELD OF THE DISCLOSURE

The present disclosure relates to radio frequency (RF) coils for magnetic resonance imaging (MRI) systems, and in particular to such coils that are covered with a removable layer of a sterile coating.

BACKGROUND INFORMATION

Magnetic resonance (MR) imaging is a known technology that can non-invasively produce images of biological structures and tissues within a subject without exposure to ionizing radiation. Images are obtained by placing at least the portion of the subject to be imaged inside a strong magnetic field (denoted by $B_0$) that is typically on the order of 1-7 T. Radio frequency (RF) coils are employed to generate precise sequences of RF energy in the form of RF magnetic field pulses (with amplitudes $B_1$) that are configured to interact with certain atoms in the subject, most commonly hydrogen atoms (e.g. single protons, commonly denoted $^1H$). Field coils are also provided that are configured to generate weaker magnetic fields having precise temporal-spatial properties (e.g., magnetic field gradient pulses) that pass through the region to be imaged. Combinations of these magnetic fields and RF pulses result in certain RF magnetic field signals emitted by the $^1H$ nuclei of molecules within the subject. Such signals can be received by the RF coils, which are sensitive to the emitted signals, and may then be mathematically processed to generate images of the internal volume of the subject.

MRI systems typically contain large RF coils, called body coils, that surround the entire subject at some distance within the main magnet bore. However, it is often desirable to obtain more precise imaging of local regions within a subject. To achieve this, local (or 'flex' or 'surface') coils can be provided. These local coils can be positioned close to or directly on the subject. The proximity and particular design of such local coils can facilitate improved image quality, wherein the design and/or selection of a particular coil configuration may be based on, e.g., the type of imaging technique used and the portion of the anatomy of interest that is being imaged. The improved image quality of local coils compared to body coils arises because the local coils are closer to the signal sources within the anatomy of interest, and because these smaller local coils are less sensitive to remote noise sources away from the region of interest.

MR can be used in certain percutaneous interventions (e.g. biopsies, thermal ablations, infiltrations) where a needle or applicator needs to be accurately placed into the target structure. MRI can provide continuous visualization of the target, surrounding sensitive structures, and of the needle/applicator as it is advanced into the subject to ensure safe and accurate placement during a procedure.

As noted above, imaging with only the large body coil may not provide sufficient image quality for such MRI-guided interventions, and local coils are typically used in such procedures. Although shapes, sizes, and configurations of local coils may vary, they may include one or more openings that are sufficiently large to facilitate insertion and manipulation of a needle (sometimes more than one needle) through such coil openings. An example of a local coil array that includes 6 individual coil elements and four coil openings near the corners of the array is shown in FIG. 1.

Because percutaneous interventions are invasive, the coil opening(s) should be of sufficient size to allow for a sterile field around the needle entry point. The sterility should not be broken by the usually non-sterile coil, e.g., to minimize the risk of infection.

Local MRI coils are often formed of multiple connected components, and may include some electronic components, such as tuning capacitors to cause them to resonate at the RF frequency of the MRI signals. Accordingly, the presence of seams, cracks, openings, internal corners, etc. in such coils, and the sensitivity of electronic components used for tuning to mechanical displacements, can make protocols for the direct sterilization of such coils problematic.

Several techniques and systems have been proposed and used to provide a sterile area around local MR coils. For example, one simple approach is to wrap sterile textile drapes around the coil and fix them with medical tape. This can be cumbersome for certain structures, such as coil arrays having multiple openings. It may be difficult to follow the contours of arbitrarily-shaped coils/arrays, and loose wrapping can cause an undesirable reduction in size of the coil openings. Sterile sheets (or 'drapes') can also be placed over a coil array, as shown in FIG. 2, to further protect the sterile environment around the coil opening. The arrow in FIG. 2 indicates the planned entry point for a needle in an MRI-guided intervention.

Another approach for maintaining sterility of local MRI coils is to provide sterile sheets that have one adhesive side. Such sheets are described, e.g., in U.S. Pat. No. 5,396,905 of Newman et al., which is incorporated herein by reference in its entirety. In this approach, a coil is "sandwiched" between two such sterile sheets, such that the sheets surround the coil and also form a continuous but penetrable barrier over the coil opening. The needle can be inserted through the sheets within the coil opening during an intervention, and the sheets can be removed and discarded after the procedure. However, proper application of such sheets can be cumbersome for some coil designs, such as the multi-element array shown in FIG. 1. Improper sealing of the sterile sheets around a coil can also break the local sterile field.

An apparatus for providing a re-usable sterile endocavity RF coil for internal use in a subject is described in U.S. Pat. No. 6,501,980 of Carlon et al., which is incorporated herein by reference in its entirety. This apparatus includes a sealed 2-piece enclosure that is structured to encase a particular coil and follow the contours thereof, and which can be epoxy-glued together to provide a sealed casing around the coil that can be sterilized. This sealed enclosure must be specifically designed for each coil that may be used, and also requires careful sterilization between uses. Also, it may not be practical for larger and/or more intricate coil structures such as that shown in FIG. 1.

Accordingly, it would be desirable to have an improved sterile local MRI coil and method for preparing such coil that addresses some of the shortcomings described above.

SUMMARY OF EXEMPLARY EMBODIMENTS

Exemplary embodiments of the present disclosure can provide sterile MRI coil arrangements and methods for producing them. In one embodiment, a local MRI coil arrangement is provided that includes a conventional local coil or coil array and a continuous coating of an applied material provided over substantially the entire outer surface of the local coil/array. Portions of a cable or lead proximal to the coil/array housing can also be covered by the material layer to maintain sterility, where the cable can be coated for a distance of at least between about 1 and 2 feet from where it attaches to the coil housing.

In one embodiment, the material layer can be provided on the coil/array in a spray form. In a further embodiment, the material layer can be applied by dipping the coil/array in a liquid material that is capable of curing, drying, solidifying, etc. to form a continuous layer on the outer surface of the coil/array. The liquid material can be provided in a tray or other container that is large enough to accommodate the coil/array being coated. Two or more successive dipping procedures can be performed, preferably with the previously-applied layer allowed to solidify or cure before applying another dipped layer. In certain embodiments, between 1 and 3 dipped layers can be applied to the coil/array. The viscosity, temperature, and composition of the liquid material can be selected to provide a uniform coating on the coil/array after it solidifies or cures.

The material layer can be made of a substance, compound, or mixture selected or formulated to be easily removable from the coil arrangement after use. The material layer can preferably be moderately adherent to the outer surface of the coil/array to prevent inadvertent removal of the material layer and unwanted exposure of portions of the underlying coil/array surface. The coating material can also be selected or formulated such that it does not leave a residue on the underlying coil/array when it is removed.

The material layer is preferably formed of a substance that can be stored and applied in a sterile condition. In certain embodiments, a liquid coating material can be provided in or with a tray that has a shape conforming to the shape of a particular coil/array, where the liquid-filled tray can be used to dip-coat the coil/array.

The coating material layer can be or include any one of a variety of substances including, e.g., a curable liquid polymer or latex. In certain embodiments, the polymer can be cured by exposure to air. In further embodiments, the coating material can be heat-curable or UV-curable.

In certain embodiments, the material layer substance can include a component to improve detachability of the material layer from the surface of the coil/array such as, e.g., gum arabic, a solvent-soluble polymer combined with small amounts of silicon or fluoride compounds, or the like.

In further embodiments, the material layer substance can include an antibacterial or antimicrobial substance. In one embodiment, the antimicrobial substance can include silver or silver ions, which may be provided in a solution. In further embodiments, the antimicrobial material substance can include triclosan, polyhexamethylenebiguanide (PHMB), or one or more other such antimicrobial agents known in the art.

A total thickness of the material layer applied to the coil/array can be between about 100 and 1000 micrometers thick. In further embodiments, the material layer can be thicker or thinner than this, based on the specific composition of the material layer.

In further embodiments, a method for producing sterile MRI coil arrangements is provided. In one embodiment, the sterile coil arrangement can be provided by spray-coating a local MRI coil/array with one or more layers of a coating material to form a continuous layer thereon, as described herein. In another embodiment, a local MRI coil/array can be dipped or submerged in a liquid coating material to form a continuous layer thereon, as also described herein. A plurality of such dipping or spraying operations can be performed to ensure that the applied material layer is continuous and completely covers the entire surface of the MR coil/array. The applied layer can include a biocide, such as an antimicrobial or antibiotic agent. In further embodiments, the applied layer can facilitate cleaning and sterilization of the coil arrangement using conventional cleaning and/or sterilizing fluids, and prevent such fluids from directly contacting the housing of the coil and any components present therein (e.g. electronic components).

BRIEF DESCRIPTION OF THE DRAWINGS

Further objects, features and advantages of the present disclosure will become apparent from the following detailed description taken in conjunction with the accompanying figures showing illustrative embodiments, results and/or features of the exemplary embodiments of the present disclosure, in which.

While the present disclosure will now be described in detail with reference to the figures, it is done so in connection with the illustrative embodiments and is not limited by the particular embodiments illustrated in the figures. It is intended that changes and modifications can be made to the described embodiments without departing from the true scope and spirit of the present disclosure as defined by the appended claims.

DETAILED DESCRIPTION OF EXEMPLARY EMBODIMENTS

The present disclosure relates to sterile local MRI coil arrangements and methods for producing them. One advantage of these coil arrangements and methods is that they can be based on virtually any existing local MRI coil, irrespective of its geometrical complexity, size, etc.

In one embodiment, a local MRI coil arrangement is provided that includes a conventional local coil or coil array. The coil arrangement further includes a continuous coating of an applied material provided over substantially the entire outer surface of the local coil/array. This layer of material may be omitted from certain portions of the coil/array such as, e.g., electrical connectors that contain conductive contacts or portions of an electrical cable or lead that extends from the coil/array. Preferably, portions of such cable or lead close to the actual coil(s) is also covered by the material layer to maintain sterility within a reasonable distance from the coils themselves, e.g., portions that extend from the body of the coil/array itself to a distance of about 1 or 2 feet from the body of the coil/array. Such distance can provide a sterile outer surface within a reasonable distance surrounding the portion of the subject being imaged by the sterile coil arrangement.

Figure 1:
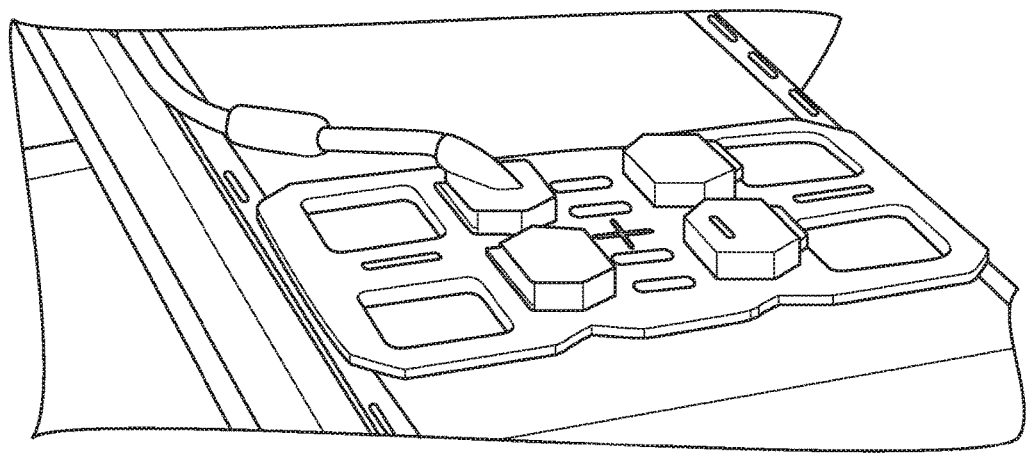
FIG. 1 is an image of a prior-art diagnostic imaging coil array that includes four access openings.
Figure 2:
FIG. 2 is an image of a prior-art simple loop coil, covered by sterile sheets, that has a large opening to facilitate access to the subject.
Figure 3A:
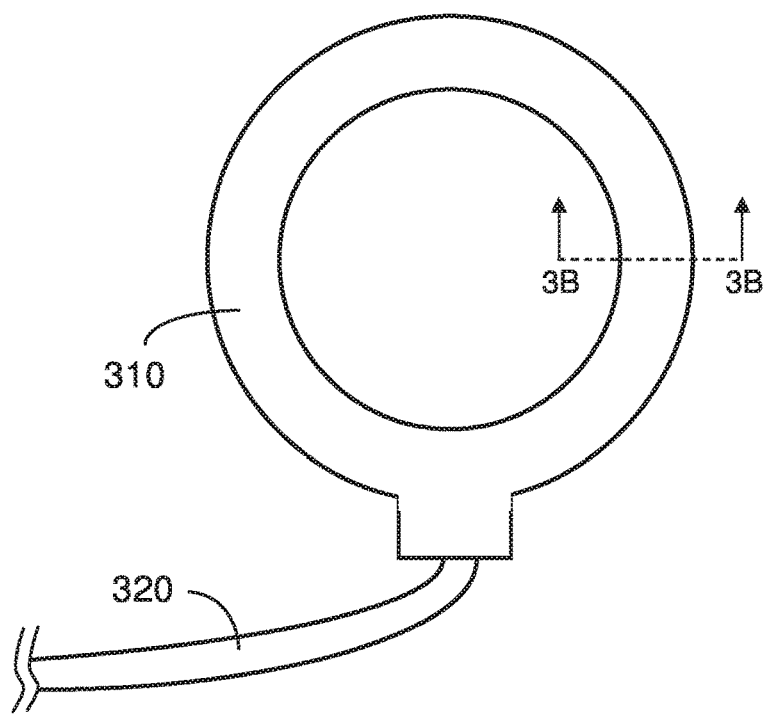
FIG. 3A is a top view of an exemplary sterile MRI coil arrangement in accordance with embodiments of the disclosure.

An exemplary sterile coil array 300 in accordance with embodiments of the present disclosure is shown in FIG. 3A. This coil array 300 includes a sterile material layer 310 surrounding the underlying housing, which may be plastic or another material, RF coil housing 310, and a conductive cable 320 extending from the housing. The cable 320 can conduct electrical signals between the internal conductive coil and an MRI system (not shown).

Figure 3B:
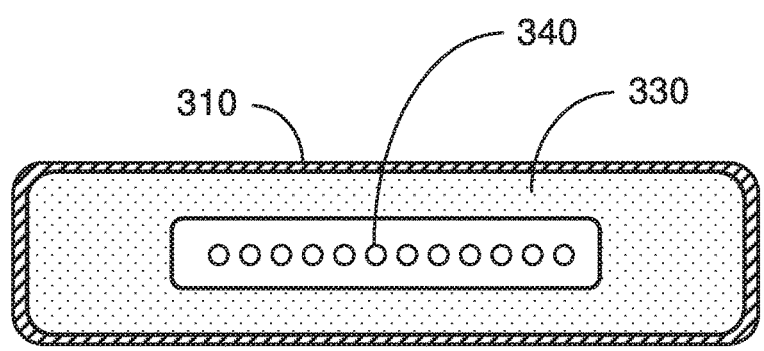
FIG. 3B is a cross-sectional view of the sterile MRI coil arrangement shown in FIG. 3A.

A cross-sectional view of the coil arrangement of FIG. 3A is shown in FIG. 3B. The coil arrangement includes a continuous outer coating of a material layer 310 that is adhered onto the underlying coil housing 330. Conductive elements 340 that form the actual RF coil are located within the housing 330. The outer material layer 310 is typically thin, and is not drawn to scale in this figure.

The continuous material layer or coating 310 can prevent liquids such as blood to penetrate the coil housing 330 and destroy electronic components that may be present therein. Furthermore, this material layer 310 can maintain cleanliness of the underlying surface of the coil/array housing 330 to extend its usable life.

The material layer 310 can be provided on the coil/array housing 330 in a spray form. This type of application can ensure that the entire surface of the coil/array housing 330 is covered by the material layer 310, including any seams, gaps, or recesses that may be present in the underlying coil/array housing 330. Such spray-coating can preferably be performed in a sterile environment, e.g., to maintain sterility of the coil arrangement 300. For example, the material layer 310 can be applied in a sterile region of the room in which the intervention will be performed, optionally a short time before the procedure begins to better maintain sterility of the coil arrangement 300.

In a further embodiment, the material layer 310 can be applied by dipping the coil/array housing 330 in a liquid material that is capable of curing, drying, solidifying, etc. to form a continuous layer 310 on the outer surface of the coil/array housing 330. The liquid material can be provided in a tray or other container that is large enough to accommodate the coil/array being coated. The depth of the liquid container should be sufficient so that the entire coil/array housing 330 can be submerged within the liquid material.

In some embodiments, a detachable handle, clamp, or the like can be affixed to a portion of the coil/array housing 330 to facilitate handling of it during the dipping procedure. To avoid discontinuities where the handle or clamp is affixed, a second dipping procedure can be performed after the first layer has solidified or cured, with the handle or clamp affixed to a different portion of the coil/array housing 330 such that the original location that it was affixed to can then be dipped and coated. In other embodiments, the coil/array housing 330 can be manipulated and dipped by grasping a distal portion of the electrical cable or lead 320 extending from the coil/array housing 330, such that the entire coil/array housing 330 and the proximal portion of the cable 320 closest to the housing can be submerged/dipped and coated with the material layer.

In this embodiment, the viscosity, temperature, and composition of the liquid material can be selected to provide a uniform coating on the coil/array housing 330 after it solidifies or cures, e.g., to provide a particular thickness of the coating layer as described below. Although multiple dipped coating layers can be applied to the coil/array housing 330, it may be preferable to coat the coil/array housing 330 with just a few layers, e.g. 1-3, to avoid extended preparation times.

The material layer, which may be applied using a spray or by dipping in different embodiments, is preferably formulated to be easily removable from the coil arrangement, e.g., after the intervention or other procedure using the sterile coil arrangement has been completed. In this manner, a fresh material layer can be provided for the coil arrangement for each sterile procedure, thereby avoiding the need to perform any additional sterilization procedures apart from applying the material layer. Properties of the material layer can also be selected such that it is moderately adherent to the outer surface of the coil/array housing 330, e.g., so the material layer does not fall off or inadvertently expose portions of the underlying coil/array housing 330 when the coil arrangement 300 is placed and manipulated before and during the intervention. Further, properties of the coating material can be selected such that it does not leave a residue on the underlying coil/array housing 330 when the coating material layer is removed.

The material layer 310 is preferably formed of a material that can be stored and applied in a sterile condition. For example, sprayable materials can be provided in a sealed spray container, e.g., as an aerosol or a pressurized-gas sprayer. Dipped-liquid coating materials can be provided, e.g., in sealed sterile containers. In certain embodiments, such liquid coating materials can be provided in or with a tray or the like that has a shape conforming to the shape of a particular coil/array housing 330. Such shaped tray can facilitate even coating of the coil/array housing 330 and may also require less of the liquid material to coat the coil/array housing 330.

The coating material layer 310 can be any one of a variety of substances in different embodiments of the disclosure. For example, the material layer 310 can be formed from or include a curable liquid polymer, latex, or elastomer. In certain embodiments, the polymer can be cured by exposure to air. In further embodiments, it can be heat-cured (e.g. using a hot-air gun or the like), UV-cured (e.g. using an ultraviolet emitter), etc. Many such curable polymers are known in the art.

In certain embodiments, the material layer substance can include a component to improve detachability of the material layer 310 from the surface of the coil/array housing 330. Such substances can include, e.g., gum arabic (natural or synthetic), a solvent-soluble polymer combined with small amounts of silicon or fluoride compounds, or the like.

In further embodiments, the material layer substance can include a biocide additive, e.g., an antibacterial or antimicrobial agent. Such agents are commercially available and can be added to various polymers and the like to help maintain sterility of the coil arrangement. For example, the antimicrobial agent can be colloidal silver, silver ions, a silver ion-containing compound, triclosan, polyhexamethylenebiguanide (PHMB), or other such agents known in the art. In further embodiments, the coating can be a hydroxyapatite-based coating that incorporates silver ions or chlorhexidine to provide antimicrobial effects. The amount of such antibacterial/antimicrobial agent that is mixed with a polymer or other coating material can be based on the particular antibacterial or antimicrobial agent and coating material used. Commercially available antimicrobial agents, for example, often have guidelines regarding what concentration is needed to be effective in different applications. Non-limiting examples of antimicrobial coating materials are described, e.g., in U.S. Patent Publication No. 2010/0062035 of Eggerstedt et al. and in U.S. Pat. No. 5,091,442 of Milner, the disclosures of which are incorporated herein by reference in their entireties.

In still further embodiments, the material used for the antimicrobial coating layer can be selected such that it has a color that contrasts with the underlying surface of the coil arrangement. Optionally, the coating material can be infused with a dye or other colorizing agent known in the art. Such colored coating material can make it easy to identify any defects or incompleteness in the coating layer after it is applied to the coil arrangement using visual inspection, to better ensure the continuity and integrity of the coating layer.

Such color can also facilitate complete removal of the coating prior to re-coating the coil arrangement, if/when the coil arrangement is re-coated, by providing easily-identifiable coating residue.

A thickness of the material layer 310 applied to the coil/array housing 330 can be fairly thin, e.g., between about 100 and 1000 micrometers thick. This exemplary thickness range can be thick enough to provide a reliable continuous layer on the coil/array to maintain sterility of the coil arrangement 300 when in use, and not be so thick that removal of the coating layer 310 after use is difficult. In further embodiments, the material layer 310 can be thicker or thinner than this, with the thickness depending on the specific substances in the material layer 310.

In further embodiments of the disclosure, a method for producing sterile MR coil arrangements 300 is provided. In one embodiment, the sterile coil arrangement 300 can be provided by spray-coating a local MR coil/array housing 330 with one or more layers of a coating material to form a continuous layer 310 thereon, as described herein. In another embodiment, a local MR coil/array housing 330 can be dipped or submerged in a liquid coating material to form a continuous layer 310 thereon, as described above. A plurality of such dipping operations can be performed to ensure that the material layer 310 is continuous and completely covers the entire surface of the MR coil/array housing 330.

In further embodiments, a method or protocol for providing sterile MRI coil arrangements can be provided. First, the MRI coil arrangement can be sealed with a continuous coating of a material. Such coating material is preferably selected to form a continuous layer over the surface of the coil arrangement, e.g., such that it can prevent contact of the coil arrangement surface with external fluids. The coating can also fill in and/or cover any cracks, seams, holes, or the like that may be present in the coil arrangement. Such continuous coating can seal the coil arrangement surface and enclosed electronic components, if present, to protect them from direct exposure to cleaning or sterilization solutions, e.g., as described below.

In certain embodiments, the coating can be applied as a sprayed-on layer of material. In further embodiments, the layer can be applied by dipping the coil arrangement into a liquid coating material, which can then be dried or cured (e.g., heat-cured or cured with UV light) to form the continuous coating layer. A plurality of coating layers can optionally be applied, e.g., to increase the thickness of the coating layer, to ensure the coating fully covers the entire coil arrangement, and/or to increase the mechanical strength of the coating layer.

A variety of materials suitable for coating MRI coil arrangements are known in the art. Such materials can be polymeric, e.g. an elastomer, and may be cured by exposure to air, by heating, by exposure to UV light, etc. In some embodiments, hydrophobic coating materials can be used, which can increase resistance to permeation of water-based fluids onto or into the coated coil arrangement. The coating material should preferably be strong enough to resist wear, tear, or rupture during such procedures as handling of the coated coil arrangement or washing/cleaning of the outer surface. As with the antimicrobial layers described above, the general coating layer can be colored or dyed with a color that contrasts with the underlying surface of the coil arrangement. Such colored coating can facilitate verification that the coating layer is continuous and more readily reveal the presence of any holes, gaps, or cracks in the coating material upon visual inspection.

The coated coil arrangement can then be cleaned and sterilized prior to use, e.g., using a conventional sterilization procedure such as application of an anti-bacterial liquid (or gas) to the outer surface of the coil arrangement. Such sterilizing fluids can include, e.g., chlorine, bleach, ethanol or another alcohol, etc. Any known and approved sterilization material or technique that does not interact with the coating material and/or does not require exposure to excessively high temperatures that may damage the coil arrangement can be used in embodiments of the disclosure.

In this manner, a method for sterilizing MRI coils for interventional procedures can be provided that includes the steps of coating the coils with a fluid-impervious layer (that is optionally bacteria-resistant) that can render the coil arrangements substantially waterproof and/or resistant to other fluids, and then cleaning and sterilizing the coated coil arrangements prior to each procedure. The coil arrangements can be cleaned following a procedure to remove any bodily fluids or other residue that may have contacted the coil arrangement during the procedure. Further, the layer can be re-applied to the coil arrangement if it appears worn or non-continuous (e.g., cracks or holes in the coating layer are seen), optionally removing the existing coating layer prior to re-coating the coil arrangement.

Embodiments of the present disclosure provide certain advantages over other sterile MR coils and methods for producing them. For example, the sterile material layer 310 can be applied to any existing local MR coil or coil array, regardless of its shape, size, or geometrical complexity. Further, application of the sterile coating layer 310 can be performed just before it is used (subject to any curing/drying time) to help maintain sterility. The sterile coil arrangements 300 described herein can also be provided without any need for external sterilization devices or systems. Also, the sterile material layer 310 can help to protect the underlying coil or coil array during use, so that the coil/array may require less frequent replacement.

The foregoing merely illustrates the principles of the present disclosure. Various modifications and alterations to the described embodiments will be apparent to those skilled in the art in view of the teachings herein. It will thus be appreciated that those skilled in the art will be able to devise numerous techniques which, although not explicitly described herein, embody the principles of the present disclosure and are thus within the spirit and scope of the present disclosure.

What is claimed is:

1. A sterile RF coil arrangement for use in magnetic resonance imaging, comprising:
    at least one RF conductive coil provided in a housing; and
    a continuous layer of a curable substance provided on the outer surface of the housing, the curable substance having a formulation including a component to assist in removal of the curable substance from the housing outer surface, the continuous layer preventing a sterilization fluid from directly contacting the housing.

2. The coil arrangement of claim 1, wherein the continuous layer has a thickness that is between 100 micrometers and 1000 micrometers.

3. The coil arrangement of claim 1, wherein the curable substance is capable of being sprayed onto the housing to form the continuous layer.

4. The coil arrangement of claim 1, wherein the curable substance is a curable liquid that can be provided on the housing by dipping the housing into the curable liquid.

5. The coil arrangement of claim 1, wherein the continuous layer comprises at least one of an antimicrobial agent or an antibacterial agent.

6. The coil arrangement of claim 5, wherein the at least one antimicrobial agent or antibacterial agent comprises at least one of colloidal silver, silver ions, triclosan, or polyhexamethylenebiguanide (PHMB).

7. The coil arrangement of claim 1, wherein the curable substance can be cured by at least one of exposure to air, exposure to UV light, and exposure to heat.

8. The coil arrangement of claim 1, wherein the curable substance has a color that is different than a color of the housing.

9. The coil arrangement of claim 1, wherein the coil arrangement comprises a plurality of continuous layers of a curable substance provided on the housing.

10. A method for providing a sterile RF coil arrangement for use in magnetic resonance imaging (MRI), comprising:
applying a continuous layer of a curable liquid substance onto a housing of an RF coil, the curable liquid substance having a formulation that includes a component to assist removal of the curable liquid substance from the housing;
at least one of curing or drying the continuous layer to form an RF coil arrangement having a fluid-resistant coating, wherein the fluid-resistant coating facilitates sterilization of the RF coil arrangement using a sterilizing fluid, and the fluid-resistant coating prevents the sterilization fluid from directly contacting the RF coil housing;
sterilizing the RF coil arrangement;
performing a first MRI procedure using the RF coil arrangement;
subsequent to the first MRI procedure, removing the continuous layer; and
repeating the steps of applying and curing or drying.

11. The method of claim 10, wherein the liquid substance is applied using a spraying procedure.

12. The method of claim 10, wherein the liquid substance is applied using a dipping procedure.

13. The method of claim 10, wherein the liquid substance comprises at least one of an antimicrobial agent or an antibacterial agent.

14. The method of claim 13, wherein the at least one antimicrobial agent or antibacterial agent comprises at least one of colloidal silver, silver ions, triclosan, or polyhexamethylenebiguanide (PHMB).

15. The method of claim 10, wherein a thickness of the fluid-resistant coating is between 100 micrometers and 1000 micrometers.

16. The method of claim 10, wherein the at least one of curing or drying comprises at least one of exposing the continuous layer to air, heating the continuous layer, or exposing the continuous layer to UV light.

17. The method of claim 10, wherein the liquid substance is applied using at least one of a spraying procedure or a dipping procedure.

18. The method of claim 10, wherein the curable liquid substance has a color that is different than a color of the housing.

19. The method of claim 10, further comprising:
applying a plurality of continuous layers of the curable substance on the housing; and
curing or drying each of the plurality of continuous layers prior to applying a subsequent continuous layer of the plurality of continuous layers.

* * * * *

UNITED STATES PATENT AND TRADEMARK OFFICE
CERTIFICATE OF CORRECTION

PATENT NO.         : 10,459,045 B2
APPLICATION NO.    : 15/082048
DATED              : October 29, 2019
INVENTOR(S)        : Arne Hengerer et al.

It is certified that error appears in the above-identified patent and that said Letters Patent is hereby corrected as shown below:

In the Specification

Column 1, prior to the Field of the Disclosure, please insert the following language:
--STATEMENT REGARDING FEDERALLY SPONSORED RESEARCH OR DEVELOPMENT
This invention was made with government support under EB007829 awarded by the National Institutes of Health. The government has certain rights in the invention.--

Signed and Sealed this
Ninth Day of June, 2020

Andrei Iancu
*Director of the United States Patent and Trademark Office*